US009554557B2

(12) United States Patent
Nehls (10) Patent No.: US 9,554,557 B2
(45) Date of Patent: Jan. 31, 2017

(54) SYSTEM FOR MARKING A NON-HUMAN BIOLOGICAL OBJECT AND FOR TAKING A SAMPLE OF THE BIOLOGICAL OBJECT (71) Applicant: Reinhard Nehls, Bocholt (DE)

(72) Inventor: Reinhard Nehls, Bocholt (DE)

(*) Notice: Subject to any disclaimer, the term of this patent is extended or adjusted under 35 U.S.C. 154(b) by 94 days.

(21) Appl. No.: 14/354,710

(22) PCT Filed: Oct. 23, 2012

(86) PCT No.: PCT/EP2012/070989
§ 371 (c)(1),
(2) Date: Apr. 28, 2014

(87) PCT Pub. No.: WO2013/060690
PCT Pub. Date: May 2, 2013

(65) Prior Publication Data
US 2015/0289477 A1    Oct. 15, 2015

(30) Foreign Application Priority Data
Oct. 28, 2011 (NL) ..................... 2007671

(51) Int. Cl.
*A61B 10/00* (2006.01)
*A01K 11/00* (2006.01)
*A61B 10/02* (2006.01)

(52) U.S. Cl.
CPC ......... *A01K 11/003* (2013.01); *A61B 10/0096* (2013.01); *A61B 10/0266* (2013.01); *A61B 2503/40* (2013.01)

(58) Field of Classification Search
CPC .............. A61B 10/0275; A61B 2010/0208; A61B 10/0266
(Continued)

(56) References Cited

U.S. PATENT DOCUMENTS 4,253,459 A * 3/1981 Willis ................. A61J 1/2089
215/341
6,419,640 B1 * 7/2002 Taylor .................. A61B 10/06
600/564
(Continued)

FOREIGN PATENT DOCUMENTS

CN 101573028 A 11/2009
CN 101917839 A 12/2010
(Continued)

OTHER PUBLICATIONS

CN 201280065116.2 Office Action dated Jan. 15, 2015.
Machine Translation of WO 2009/010658 A2.

*Primary Examiner* — Daniel Cerioni
(74) *Attorney, Agent, or Firm* — Hoffmann & Baron, LLP (57) ABSTRACT A system for marking a non-human biological object and removing a sample of the biological object includes a first tag part, a second tag part, a pin connected to the first tag part by its first end and provided with a head at its second end, a sample removing stopper which, while attaching the tag parts on the biological object and removing the sample therefrom, is positioned on the head of the pin. The stopper has a cutter at its front, which cutter delimits a sample receiving cavity. The second tag part is provided with a passage for the stopper and the head of the pin. The second tag part is provided in the region of the passage of the second tag part with a sample fixating spike member.

21 Claims, 5 Drawing Sheets (58) Field of Classification Search
USPC .......................................................... 600/567
See application file for complete search history.

(56) References Cited

U.S. PATENT DOCUMENTS

| | | |
|---|---|---|
| 7,772,979 B2 | 8/2010 | Caisley |
| 8,858,568 B2 | 10/2014 | Nehls et al. |
| 2002/0137033 A1 | 9/2002 | Brem |
| 2005/0049520 A1* | 3/2005 | Nakao .................... A61B 10/06 600/562 |
| 2008/0044313 A1 | 2/2008 | Caisley |
| 2009/0326548 A1 | 12/2009 | Nehls et al. |
| 2010/0210011 A1 | 8/2010 | Hilpert et al. |
| 2011/0000111 A1 | 1/2011 | Hilpert et al. |
| 2011/0041367 A1 | 2/2011 | Bladen et al. |

FOREIGN PATENT DOCUMENTS

| | | |
|---|---|---|
| CN | 102014613 A | 4/2011 |
| CN | 102047849 A | 5/2011 |
| CN | 201894108 U | 7/2011 |
| CN | 201967479 U | 9/2011 |
| CN | 201995439 U | 10/2011 |
| WO | 0239810 A2 | 5/2002 |
| WO | 2006000869 A2 | 1/2006 |
| WO | 2008055690 A1 | 5/2008 |
| WO | 2009010658 A2 | 1/2009 |

* cited by examiner

SYSTEM FOR MARKING A NON-HUMAN BIOLOGICAL OBJECT AND FOR TAKING A SAMPLE OF THE BIOLOGICAL OBJECT

CROSS-REFERENCE TO RELATED APPLICATIONS

This application is the National Stage of International Application No. PCT/EP2012/070989 filed Oct. 23, 2012, which claims the benefit of Netherlands Application No. 2007671, filed Oct. 28, 2011, the contents of which are incorporated by reference herein.

FIELD OF THE INVENTION

The invention relates to marking of a non-human biological object and at the same time removing a sample of the biological object.

In particular, the invention relates to the marking and taking a sample of animals. However, the invention also relates to the marking and sampling of other non-human biological objects, such as plants.

The marking has at its main purpose to identify the object, as is in particular done for livestock.

BACKGROUND OF THE INVENTION

In the past few years, the desire and need to reliably identify individual animals has been increasing further. Particularly if the animals' meat is intended for human consumption or if the animals are going to be part of the human consumption chain in some other way, there is a need for reliable identification. One example is the BSE problem, where the accurate determination of the origin and the life history of the animals are of importance. However, the reliable identification of animals also is desired for animals that are not destined for consumption, but e.g. is a pet, (race) horse, or the like.

The invention relates to a system which not only provides for a tag, such as an eartag, to be attached to the animal, but also achieves the simultaneous removal and storage of a sample of biological material from the animal. The removal of a small sample of the biological material and storage thereof in the sample container can have various purposes, e.g. identification of individual animals based on the "genetic fingerprint" which can be determined using the sample taken. The removed sample can also be used for other purposes, such as that one or more test are performed on the sample, e.g. molecular genetic tests, blood test(s), etc.

Such systems are known, inter alia, from WO 02/39810, WO 2006/000869, and WO2009/010658.

In presently marketed systems the stopper has a circular cutter at its front with a cutting ring made of metal. This cutter delimits a sample receiving cavity which is open at the front. The cutter removes a sample from the object with a diameter of about 4 to 5 millimeters. An issue relating to the practical use of such tagging and sampling systems is the sampling failure rate. In practice specialized laboratories receive the filled and closed sample containers from farmers and check whether a sample is actually present in the sample container. If no sample is present in the container, the laboratory informs the farmer that no sample is present and requests that a new sample is taken from the same animal. Even at failure rates between 0.5 and 1.5% this means an undesirable effort for the laboratories and farmers in view of the enormous number of animals that are to be tagged and sampled with these systems.

OBJECT OF THE INVENTION

The present invention aims to provide measures that allow for a reduction of the sampling failure rate in these systems.

SUMMARY OF THE INVENTION

The invention provides a system which is characterized in that the second tag part is provided in the region of the passage of the second tag part with a sample fixating spike member having a spike directed away from the sample container, the sample fixating spike member being secured in an initial position thereof to the second tag part such that when the cutter is pressed onto one side of the object the spike is directed towards the sample receiving cavity of the stopper and engages on the opposite side of the sample to be removed from the object thereby fixating said sample to be removed, and the sample fixating spike member being movable away from said initial position into the sample container under the load of the sample when the cutter is continued to be pressed onto the opposite side of the object.

The invention is based on the insight that in everyday practice, especially when applying such systems as ear tags on livestock animals, the ear tissue is sometimes not cut by the cutter in neat circular fashion as in a cookie cutter but remains partly connected to the rest of the ear and then slips from underneath the front end of the cutter.

By the provision of the spike that engages on the ear on the side opposite from the side where the cutter engages, the ear, in particular the sample to be removed, is pressed onto the spike and effectively fixated by the tip of the spike. This effectively counteracts the undesired slippage of this portion of the ear and allows the cutter to perform its cutting function. In addition the spike presses onto the sample and facilitates the (partial) entry of the sample into the sample receiving space of the cutter.

As the sample fixating spike member—in its initial position—essentially stands in the path that the sample and the stopper with the cutter make towards the sample container, the invention proposes that the spike member is movable away from said initial position, into the sample container under the load of the sample when the cutter is continued to be pressed onto the opposite side of the object.

In an embodiment one could envisage that the spike member is designed as a brittle component that effectively crumbles or shatters under the pressing load exerted thereon by the sample after having initially resisted said loading, e.g. the spike member being partly or entirely made of glass or a brittle plastic material. The remains of the spike member will then be pushed by the sample into the sample container. For example, the spike member can be made, preferably by injection moulding, from a brittle polystyrene, as traded under the name POLYSTYROL. For example one could use a so called crystal polystyrene that is transparent and colourless. The crumbling or shattering of the brittle component could be in unspecified pieces, but one can also envisage the provision of predetermined fracture initiation formations, e.g. formed by a groove or other recess in the spike member, that will cause the brittle spike member to start shattering from one or more predetermined locations.

Design the spike member as a brittle component that effectively shatters after having in initially resisted the loading thereof has as an advantage—compared to a spike member that remains substantially intact during the application of the tag and the taking of the sample—that the remaining pieces do not from an undue obstacle within the sample container when later in a laboratory the sample is processed, e.g. when a needle is pierced through the sample container body in the processing routine.

The brittle version may thus be embodied to shatter already during the sample taking and storage process, but one could also envisage that a brittle version of the spike member has sufficient strength to remain intact in this process and is only shattered during a later stage in a laboratory when a needle or the like is pierced through the container or stopper, the needle colliding with the spike member and then shattering the spike member.

In another more preferred embodiment the sample fixating spike member is secured in an initial position thereof to the second tag part via a temporary retaining connection, such that when the cutter is pressed onto one side of the object and the sample presses onto the spike member, said spike member is pressed from its initial position to slide into the sample container. As is preferred a threshold load needs to be overcome to release the temporary connection.

In an embodiment the sample container has an open, non-sealed introduction opening, and the spike member is embodied as a closure of the passage in the second tag part when the spike member is in its initial position. The spike member thus performs a sealing function in its initial position, e.g. avoiding the ingress of contaminants into the sample container.

In another, less preferred, embodiment the sample container is sealed at its introduction opening by a penetrable film or membrane. The spike member may then be provided at the side facing said film or membrane with one or more cutting formations, e.g. a circular cutter edge, enhancing the penetration, or even causing circular cutting, of said film or membrane.

In an embodiment the spike member may effectively protrude significantly in front of the surrounding face of the second tag part, against which face the object comes to lie.

However, in view of a preferred minimum effective height of the spike member of at least 3 millimeters, this arrangement would create a less desirable embodiment as the protruding spike can be seen as potential hazard for the animal and possibly for the person applying the tag onto the animal.

It is therefore a preferred embodiment that the spike member has a body with a base and a tip, wherein—in the initial position—the base is recessed in the passage of the second tag part with respect to the entry opening of said passage for the stopper and the head. This recessed arrangement may be such that—in the initial position—the tip of the spike is located in or near the plane of the entry opening, e.g. within 2 millimeters in front of or behind said plane, and one or more spaces are left open around said spike member, between said spike member and the second tag part. The ear tissue will in this arrangement be pressed partly into said space or spaces between the spike member and second tag part, so that the spike still is effective even though is does not, or only little, protrude in front of the second tag part.

In an embodiment the spike member has a base that is adapted to slidingly fit in the sample container. The sliding fit may be designed to create a resistant force such that the spike member must be continuously forced into the sample container until it reaches it final position, and thereby keeps pressing against the sample during its insertion into the sample container. This may contribute to a lowering of the sampling failure rate and also more or less positions the sample within the sample container.

In an embodiment the spike member is embodied as an openable capsule forming at least one sealed compartment therein filled with a functional compound, said capsule being adapted to open upon introduction of the spike member, sample, and stopper into the sample container, thereby bringing said functional compound in communication with the sample. Such "functional compounds" can be for example one or more preservatives, dehydrating agents and/or reacting agents. Possible embodiments of the openable capsule as well as the sample container are disclosed in WO2008/055690, which corresponds to US 2009/0326548 A1, both of which are incorporated herein by reference.

It is noted that the functional compound need not be retained in a compartment of the capsule but may also be embodied as a solid body, e.g. with a binding agent to form a solid body, the solid body e.g. being placed in the container or assembled to the spike member.

In an embodiment—in the initial position—the spike member is secured via one or more frangible bridges, e.g. to a retaining ring embedded in the second tag part or a retaining ring clamped between the second tag part and the sample container, said one or more frangible bridges breaking to allow the spike member to move away from its initial position.

In another embodiment—in the initial position—the spike member is clampingly retained in the passage opening and/or in the sample container. In an embodiment wherein the spike member is adapted to slide into the sample container, the load onto the spike member then is envisaged to cause the spike member to move away from initial position.

In another embodiment—in the initial position—the spike member is secured via one or more deformable connection members, e.g. a deformable circumferential flange clamped between the second tag part and the sample container, said one or more deformable connection members deforming under load applied by the sample onto the spike member and thereby releasing the spike member. For example a hard plastic spike member is provided with a flexible plastic circumferential flange clamped between the second tag part and the sample container, so that the flange slips from between the tag part and the container as the spike member is moved into the sample container. A similar functioning embodiment could be made e.g. from thin metal plate material.

In an embodiment the spike member is at least partly made of transparent plastic, e.g. so as to allow for inspection of the content of the filled sample container.

In an embodiment the spike member has a body with a base and a tip, wherein the effective height of the spike member above the base is at least 3 millimeters, preferably between 4 and 7 millimeters. Such an effective height allows for a reliable engagement with the sample.

In an embodiment the spike member has a conical sample engagement portion having an outer diameter reducing towards the tip of the spike member.

In an embodiment the spike member has a base and the sample container has an abutment for said base, the spike member being slideable towards said abutment upon introduction of the spike member, sample, and stopper into the sample container so as to contact said abutment.

In an embodiment the spike member is embodied as an openable capsule filled with a functional compound, e.g. having one or more wall portions that fracture upon contact of the spike member with said abutment in order to bring the sample into communication with said compound.

In an embodiment the spike member is embodied as an openable capsule filled with a functional compound, and the sample container includes one or more piercing members arranged to pierce said capsule upon introduction of the spike member, sample, and stopper into the sample container, in order to bring the sample into communication with said compound.

In an embodiment the spike member is embodied as an openable capsule filled with a functional compound, wherein the capsule slidingly fits in said sample container, and wherein the capsule is embodied to open on a side opposite from the spike member, and wherein one or more communication passageways are present between the capsule and the sample container, e.g. one or more grooves in a section of the sample container wall, thereby establishing communication between the sample on one side of the spike member and the functional compound.

For example a functional compound servers to stabilise the DNA of the sample, e.g. protect the sample against DNA-degrading enzymes. For instance said substance is a hygroscopic substance serving to dry the sample.

It will be appreciated that the functional compound can have any suitable composition both in chemical and in physical form, e.g. as a granular or powdery material, as a liquid, a gel, a solid (e.g. a tablet), a gas, an emulsion, etc. It is possible that the functional compound is arranged in a compound container attached to the spike portion of the spike member. The compound container can also have a porous or permeable wall or a porous or permeable wall part, which compound container is preferably arranged in the capsule.

The chemical composition of the one or more functional compounds can be selected based on the desired effect of the compound on the sample. For instance the compound can be a reagent, a preservative or a dehydrating agent, such as a molecular sieve, salt, silica gel, a compound for lysing the cells of the sample and/or a compound for eluting the sample tissue for obtaining RNA. Many suggestions for functional compounds have already been presented in prior art as suitable for samples of biological objects and new developments, e.g. in the field of genetics, blood testing, etc, will likely produce new functional compounds all of which can be retained in a suitably designed openable capsule.

The embodiment of the spike member as an openable capsule, which is manufactured and filled as an item distinct from the sample container, is beneficial for the manufacturing process of the system, e.g. as no functional compound has to be filled directly into the sample container. Also the properties of the material spike member as well as the design of said spike member can be selected independent from the sample container, so that each item can be optimised for its function and practical use.

In this respect it is noted that the material of the spike member (or part of said spike member) can be selected to be hard and rigid, possibly frangible, e.g. of brittle material, whereas the sample container should commonly be relatively flexible, so as to be strong and tough to resist damage during handling.

Also such sample containers with samples held therein might be stored for a long time at low, freezing temperature. Plastic material, which is the preferred material for the body of the sample container, which is suited for such conditions preferably has a high impact resistance and thus is less suited to serve as material for the spike member.

In an embodiment the spike member is recessed in the passage of the second tag part and a cover is placed over the entry opening of said passage, said cover e.g. being penetrable or being removable prior to application of the tag system. The cover may be formed as an integrally moulded thin and penetrable wall part of the second tag part, spanning across the passage for the stopper and the head.

In such embodiments one could envisage that the spike member is perforated and that a functional compound is present on the side of the spike member facing the container or in the container. Upon application of the tag system, the sample would then come into communication with the compound via the one or more perforations in the spike member.

The invention as well as advantageous embodiments of the invention are described in the subclaims and in the following description with reference to the drawing.

DETAILED DESCRIPTION OF THE INVENTION

Below, a first exemplary embodiment of all parts of the system for marking a biological object, in particular for ear-marking an animal, and for taking a sample of the biological object according to the invention will be described with reference to FIG. 1a-c.

As the invention is focussed on the spike member some of the further drawings will not show the tag parts.

It is noted that those skilled in the art can take possible embodiments, details, variants, etc, as well as information regarding the method of application of the system, as well as potential use of the sample stored in the sample container from prior art documents in this field, e.g. as mentioned herein before.

The system illustrated comprises a first tag part 1, a second tag part 2 and a pin 3. The pin 3 has a first end and a second end, the pin 3 being connected to the first tag part 1 by its first end. The pin is provided with a head 4 at its second end. The pin 3 can be integrally moulded with the first tag part 1.

The system shown furthermore comprises a stopper 20 as will be explained in more detail below.

The second tag part 2 is provided with a passage 5, such that the pin 3 with the stopper 20 arranged on its head 4 can be pressed through a part of the biological object, in particular through the ear of an animal, and subsequently into and through the passage 5 of the second tag part 2, as a result of which the first and second tag parts 1, 2 are attached to one another and to the biological object via the pin 3.

It is noted that the tag parts can have a different design than shown here, and many embodiments are known in the art.

The system furthermore comprises a sample container 10 with an introduction opening 11 for introducing the stopper 20 with the sample of biological material of the object into the sample container 10, which sample container 10 is attached to the second tag part 2 (see FIG. 1) via a releasable connection, e.g. a snap connection, in such a manner that the opening 11 of the sample container 10 and the passage 5 of the second tag part 2 lie in line.

As is preferred a flange edge 12 of the sample container 10 is releasably held in a raised annular wall 7 of the second tag part 2.

While the pin 3 is being pushed through the object, the stopper 20 is on the head 4 of the pin 3, in such a manner that a sample 8 of the biological object is taken while the pin is being pushed through the biological object and said sample is introduced into the sample container 10, following which the opening 11 of the sample container 10 is directly sealed by the stopper 20. At the same time, the stopper 20 may detach from the head 4 of the pin 3.

In the embodiment shown the stopper 20 has a circular cutter 21 at its front. Here the stopper 20 has a plastic body provided with a metal cutting ring 23. The cutter 21 delimits a cavity 22 which is open at the front and in which the sample will mainly be received. As is common the diameter of the cutter 21 is between 3 and 5 millimeters, here about 4 millimeters.

It is noted here that said stopper 20 could have a different embodiment. Examples thereof are shown in mentioned prior art documents and the skilled person will readily understand how to combine said stoppers with the measures according to the invention.

Figures 1A, 1B, 1C:
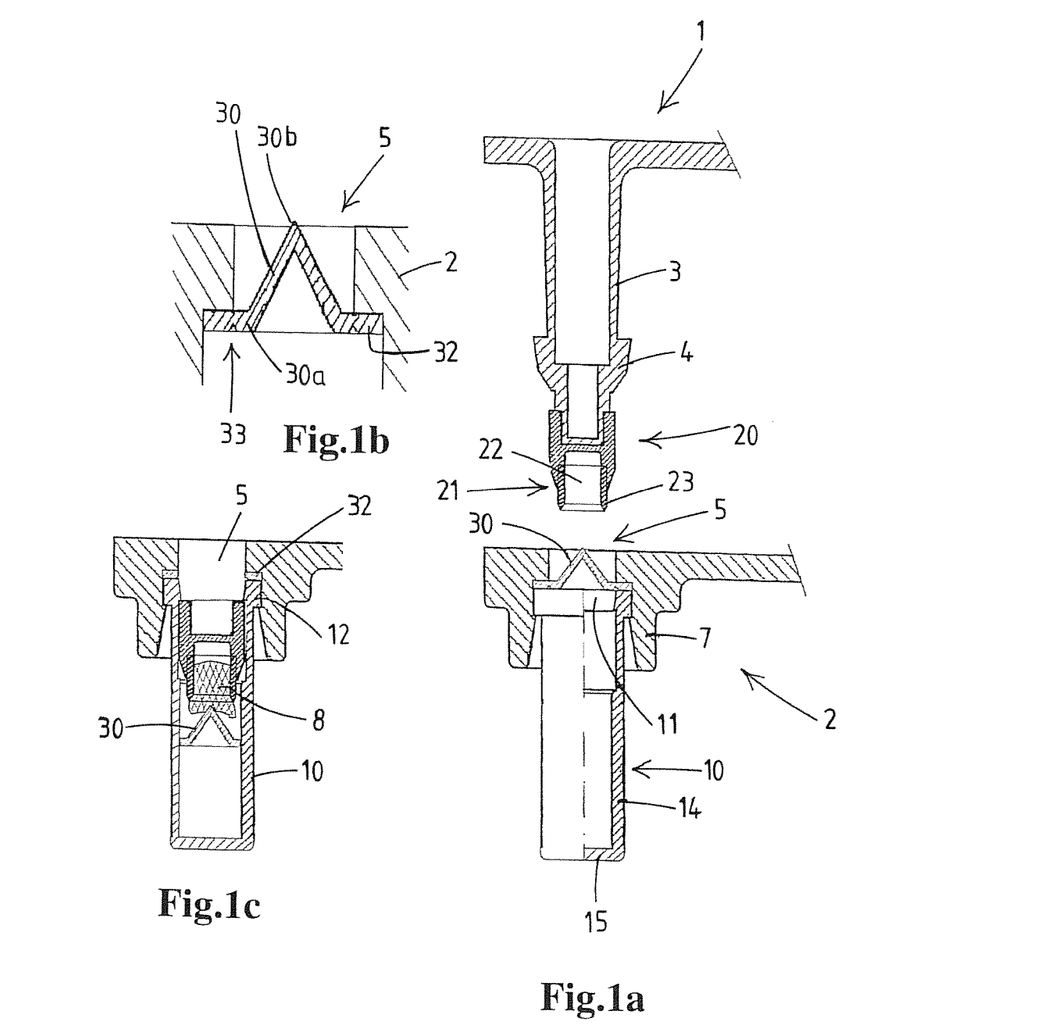
FIGS. 1a-c show an example of the system according to the present invention, including a first ear tag part provided with an integral pin and a releasable stopper, and a second ear tag part with a spike member and a sample container.

In a preferred embodiment, as illustrated in FIG. 1, the sample container 10 comprises a body, for example produced by injection-moulding a suitable plastic, with a peripheral wall 14 and the opening 11 at one axial end and an integrally formed bottom 15 at the opposite axial end.

The body of the sample container 10 is preferably non-transparent, for example made from POM or polyamide.

The stopper 20 can be transparent in order that the introduction of a sample into the sample container 10 can be checked visually. The stopper 20 is preferably injection moulded from suitable plastic and can, for example, be made from PC (polycarbonate), PS (polystyrene), PMMA.

The metallic cutter ring 23 is preferably embedded in the stopper 20 upon injection moulding.

The second tag part 2 is provided in the region of the passage 5 with a sample fixating spike member 30 having a spike directed away from the sample container 10.

The spike member 30 is secured in an initial position (see FIGS. 1a, b) thereof to the second tag part 2 such that when the cutter 21 is pressed onto one side of the object (not shown) the spike is directed towards the sample receiving cavity 22 of the stopper 20 and engages on the opposite side of the sample to be removed from the object thereby fixating said sample to be removed.

The sample fixating spike member 30 is movable away from said initial position into the sample container (see FIG. 1c) under the load of the sample when the cutter 21 is pressed onto the opposite side of the object.

The spike member 30 is secured in the initial position thereof to the second tag part 2 via a temporary retaining connection, such that when the cutter 21 is pressed onto one side of the object and the sample presses onto the spike member 30, said spike member 30 is pressed from its initial position to slide into the sample container.

The sample container 10 has an open, non-sealed introduction opening 11. The spike member 30 is embodied as a closure of the passage 5 in the second tag part 2 when the spike member 30 is in its initial position.

As can be seen the spike member 30 has a body with a base 30a, here annular, and a tip 30b, wherein—in the initial position—the base 30a is recessed in the passage 5 with respect to the entry opening of said passage 5 for the stopper and the head.

The tip 30b—in the initial position—is located in or near the plane of the entry opening, e.g. within 2 millimeters in front of or behind said plane. Here the tip 30b is slightly in front of said plane, but a recessed position of the tip is also possible.

The base 30a has a diameter such that said base slidingly fits in the sample container 10.

A retaining ring 32 is clampingly placed between the container 10 and the second tag part 2, and the spike member 30 is—in the initial position—secured via one or more frangible bridges, here a circumferential bridge 33 with a diameter corresponding to the diameter of the introduction opening, to the retaining ring 32.

As is preferred the spike member 30 and the retaining ring 32 are manufactured as a monolithic component, preferably of plastic. The one or more bridges are preferably formed during the injection moulding but can also be formed later, e.g. by cutting, etc.

As can be seen in FIGS. 1a-c the bridge 33 is designed to break or fracture as the load thereon surpasses its breaking strength. The load is caused by the sample pressing onto the spike member 30, which is in turn caused by the cutter pressing onto the opposite side of the ear.

As is preferred the spike member 30 has a body with a base and a tip, wherein the effective height of the spike member above the base is at least 3 millimeters, preferably between 4 and 7 millimeters.

As is preferred the spike member 30 has a conical portion above the base 30a having an outer diameter reducing towards the tip of the spike member. As is preferred the conical portion is hollow, but a rigid conical portion is also envisaged.

The spike member 30 is pressed into the container 10. As is preferred the fit is such that this motion is resisted so that the spike member continues to be pressed against the sample 8 during this motion towards its final position in the container 10, or—in a brittle version of the spike member—until it shatters, e.g. when being obstructed by an annular shoulder within the container or otherwise.

In a variant the container has an abutment for the base 30a at a predetermined position, possibly a shoulder in the wall of the container or another obstacle, possible the bottom of the container. The spike member 30 is slideable towards said abutment upon introduction of the spike member, sample, and stopper into the sample container so as to contact said abutment. This may allow to keep the sample in a predetermined section of the sample container. It may also be used to keep the sample in contact with the spike member.

It is noted that the release of the retaining ring 32 may not need the provision of dedicate breakable bridges if the base itself is designed to be fractured, e.g. due to a suitable selected material and/or thickness.

As will be appreciated, once the sample 8 is in the container as shown in FIG. 1c, the closed container can be readily detached from the second tag part 2, e.g. for shipping to a laboratory.

As explained the presence of the spike member 30 contributes to a lowering of the sampling failure rate, as the sample 8 is in the process of application of the tag parts to the ear or other object fixated, e.g. impaled, on the spike member, thus hindering or inhibiting sideways motion that would allow for the sample not being properly removed and introduced into the container 10.

In a design of the spike member 30 as a closure, no closure is needed on the container 10 at the introduction opening. This facilitates the manufacturing process of the system. Also drawbacks of the known film closure, such as interfering with the proper sealing by the stopper 20 as the film may become wedged between the closure and the stopper, are avoided.

In an alternative embodiment—in the initial position—the spike member 30 is secured via one or more deformable connection members, e.g. if the ring 32 is embodied as a deformable circumferential flange of the spike member that is clamped between the second tag part and the sample container. These one or more deformable connection members are then envisaged to deform under load applied by the sample onto the spike member and thereby release the spike member to move into the sample container 10. For example the circumferential flange 32 of the spike member is embodied as a flexible portion, e.g. by making it of a relatively flexible plastic and the base and spike of the spike member as a relatively hard plastic, e.g. in a 2K-injection moulding process.

Figure 2:
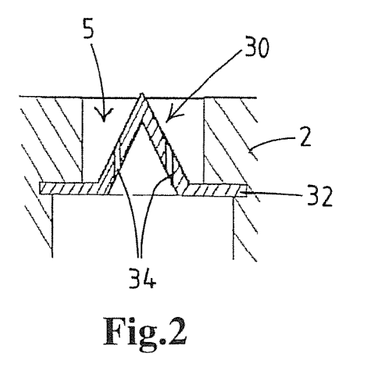
FIG. 2 shows a portion of the second tag part and another embodiment of the spike member.

In FIG. 2 an embodiment is shown wherein the spike member 30 is perforated to allow for communication between the front and rear side of the spike member 30. This is e.g. envisaged for an embodiment where a described film closure is provided on the container, or in embodiments wherein this perforation allows for communication between the sample 8 and a compound filled in the container. The perforations may be one or more channels formed in the spike member during injection moulding.

FIG. 2 also illustrates the idea to embed the retaining ring 32 (formed here integrally with the spike member 30) in the second tag part 2, preferably during injection moulding of the second tag part.

The spike member 30, possibly including the retaining ring 32, may be embodied as a unitary (plastic) member with a reinforcement collar member that is to be embedded in the second tag part to reinforce one or more portions of the second tag part, e.g. the collar 7 thereof when present.

Figure 3:
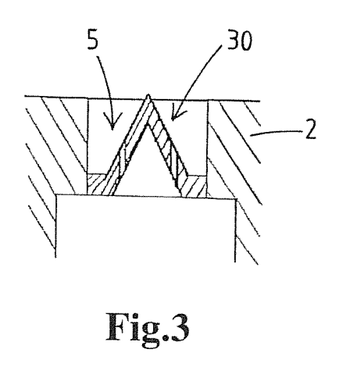
FIG. 3 shows a portion of the second tag part and another embodiment of the spike member.

In FIG. 3 it is illustrated that the spike member 30 is—in the initial position—clampingly retained in the passage 5, e.g. the spike member 30 being of a relatively hard material. For example the member 30 is press fitted in the passage 5 of second tag part 2.

Figure 4:
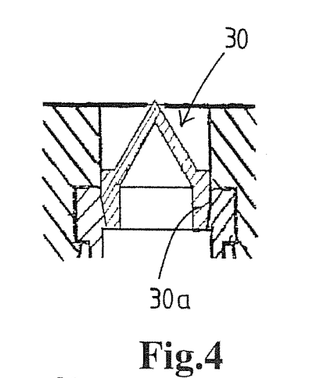
FIG. 4 shows a portion of the second tag part, the container, and another embodiment of the spike member.

FIG. 4 illustrates that the spike member 30 is fitted—in the initial position—both in the passage 5 and in the sample container 10. Here the spike member 30 has a base embodied as a skirt that fits into both the passage 5 and the container 10.

The spike member 30 may have a tapering base 30a (as e.g. in FIG. 4) that—in the initial position—fits in a corresponding seat of the second tag part and/or of the container, the taper providing some resistance against the spike member 30 being pressed (further) into the container 10. A similar effect can be obtained by other designs wherein the spike member has a portion of greater diameter that must overcome a narrower diameter portion of the seat in either the passage and/or the container.

Figure 5:
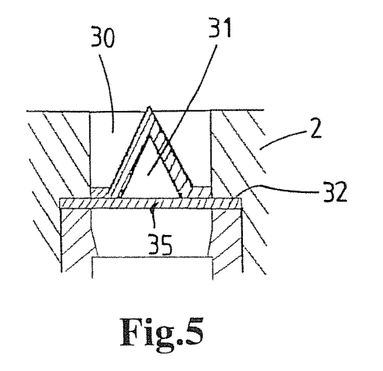
FIG. 5 shows a portion of the second tag part, the container, and another embodiment of the spike member.

FIG. 5 illustrates a spike member 30 embodied as an openable capsule forming at least one sealed compartment 31 therein filled with a functional compound. This capsule is adapted to open upon introduction of the spike member, sample, and stopper into the sample container, thereby bringing said functional compound in communication with the sample.

In this example it is envisaged that the pressure on the spike member will after an initial period of resistance, cause a fracturing of the body of the spike member and release from the retaining ring 32. For example the plate member 35 of the base that extends underneath the cone spaced space 31 will bend and fracture, also causing fractures in the conical wall of the spike member and/or along the circumferential flange portion of the base 30a.

Figure 6:
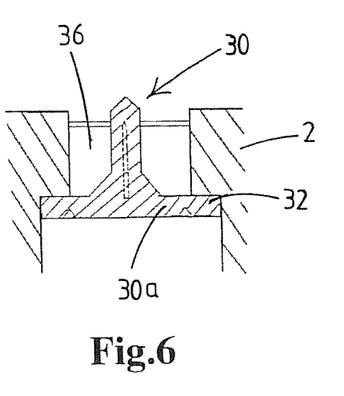
FIG. 6 shows a portion of the second tag part, and another embodiment of the spike member.

FIG. 6 illustrates an embodiment of the spike member 30 with a column extending in the passage and having a conically pointed end with a sharp tip. The column extends from a base 30a in the direction of the cavity 22 when the tag system is applied to an animal ear or other object.

As shown in FIG. 6, provision may be made for one or more spike stabilizing fins 36 in the space between the spike and the wall defining the passage 5, e.g. three or four fins at different angular positions. The fins 36 may have a sharp edge facing away from the container. The spike extends beyond the fins 36 to obtain the desired fixation effect.

Figure 7:
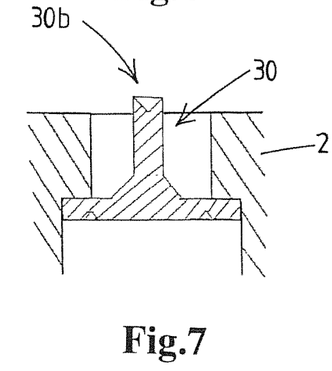
FIG. 7 shows a portion of the second tag part, and another embodiment of the spike member.

FIG. 7 shows a spike member 30, wherein the spike has an inverted cone shaped recess at its tip.

Figures 8A, 8B, 8C:
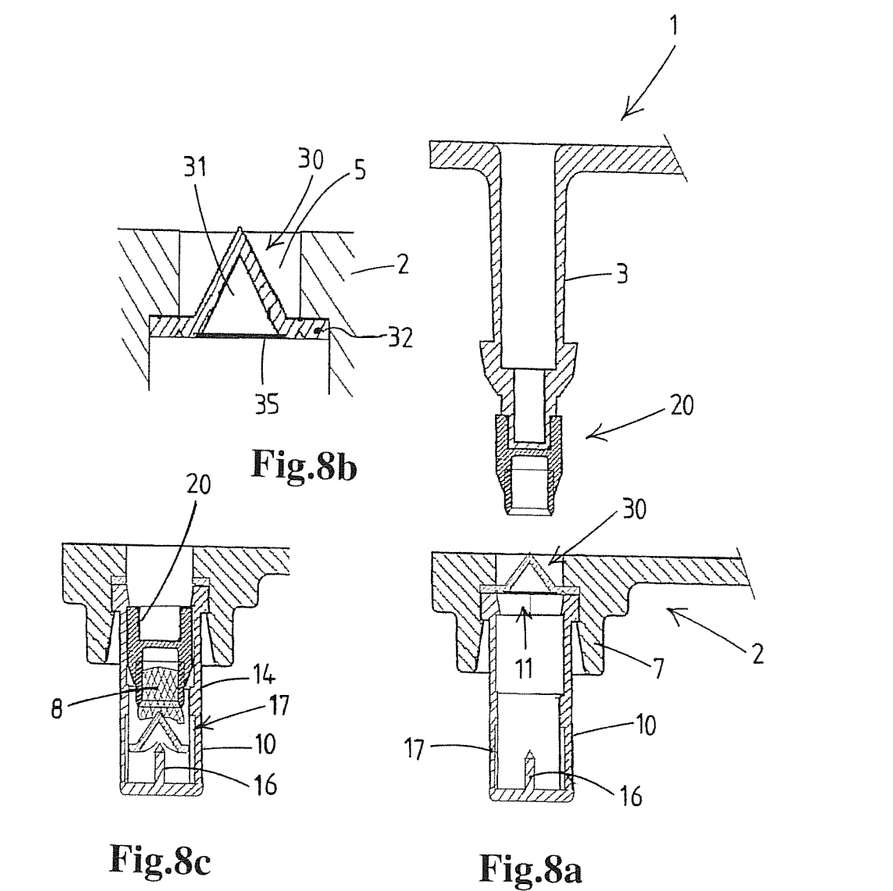
FIGS. 8a-c show a further example of the system according to the present invention, including a first ear tag part provided with an integral pin and a releasable stopper, and a second ear tag part with a spike member and a sample container.

FIGS. 8 a-c illustrate a system wherein the spike member 30 is embodied as an openable capsule contains a functional compound, and preferably also acting as closure of the passage 5; the container 10 not having a film or other seal.

Here the spike member 30 has a compartment 31 that is closed at the side of the container 10 by a frangible wall 35, here a foil seal, to contain the functional compound in the spike member.

In the initial position the spike member 30 is secured to a retaining ring 32

The spike member 30 now embodied as capsule slidingly fits in the sample container 10.

The capsule 30 is embodied to open on a side opposite from the spike member, by breaking the wall 35.

Here it is illustrated that the container has a piercing member 16 arranged to pierce the capsule 30, here wall 35, upon introduction of the spike member, sample, and stopper into the sample container.

In order to establish communication between the sample 8 on one side of the spike member 30 and the functional compound on the other side one or more communication passageways are present between the capsule and the sample container, here one or more grooves 17 in a section of the sample container wall 14.

As is preferred a spike member 30 is at least partly made of transparent plastic.

In another capsule embodiment (not shown) the capsule will abut in a final position on an abutment of the container 10, e.g. the bottom, prior to the stopper reaching its final position in the stopper. Continued pressure on the capsule may then cause the capsule to fracture, e.g. the spike being pressed further into the container so as to cause fracturing around the foot of the spike and so as to bring the compound into contact with the sample 8.

Figure 9A:
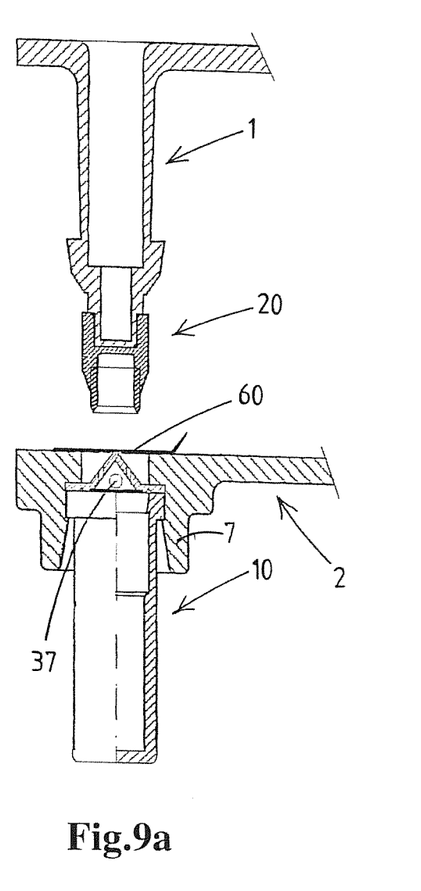
FIGS. 9a-c show a further example of the system according to the present invention, including a first ear tag part provided with an integral pin and a releasable stopper, and a second ear tag part with a spike member and a sample container, FIGS. 10a, b illustrate the behaviour of the spike member in the system of FIG. 1 when the spike member is made from brittle material.
Figure 9B:
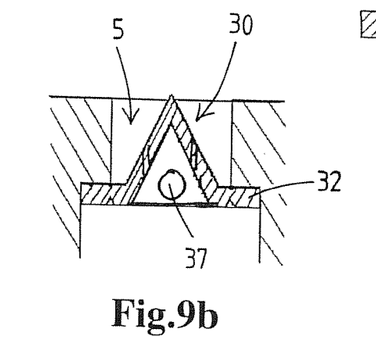
Figure 9C:
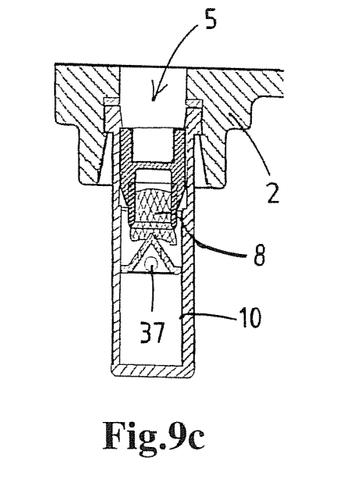

In FIG. 9a the entry opening of the passage 5 is sealed by a cover 60, here a user removable adhesive cover (with a lifting tab to facilitate removal). The cover effectively hides the spike member 30 from view. In an alternative the cover is a penetrable cover, e.g. a film that ruptures are the tag system is applied and the ear presses the film into the passage 5. The spike member 30 then aids in the rupturing of the cover.

If the cover 60 is embodied as an airtight closure, one can envisage (as depicted here) that the spike member 30 is perforated so that the spaces on the front and the rear of the spike member are in communication via the perforations. Also a functional compound can then be present in the container. In another embodiment—as shown here—the spike member 30 is provided with a compartment containing a functional compound (see at 37) which is then in open communication with the side of the spike facing the sample 8.

In the embodiments shown in the drawings the spike member could be made from a brittle material, e.g. from brittle polystyrene, and embodied so that the spike member shatters in defined or undefined pieces after having initially stayed intact to perform its fixating function. The remains of the spike member will then be pushed by the sample into the sample container.

Figure 10A:
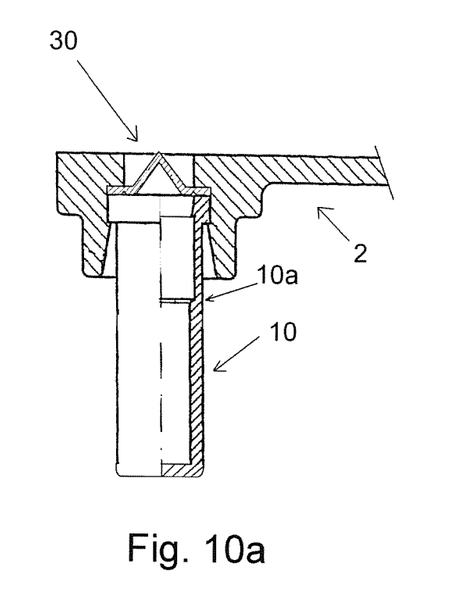
Figure 10B:
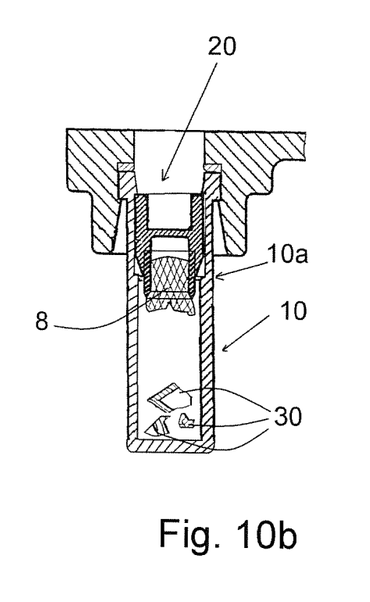

This idea is illustrated by way of example only in FIGS. 10a, b wherein the spike member 30, after having served its fixation purpose at least during the cutting of the sample 8 from the ear, is shattered into fragments (see bottom of container in FIG. 10b). The shattering is due to the load on the spike member as it is pushed deeper into the container during the sample taking process. This shattering may be enhanced by having a restricted passage within the container 10 that causes the spike member to be stressed beyond its breaking strength. For example this can be done by shoulder 10a within the container at a position remote from the open end, e.g. the same shoulder 10a that serves to block the stopper 20 from further motion into the container 10 one the stopper is fully received in the container 10. If desired another obstacle formation of the container located in the path of the spike member could serve the same purpose, e.g. a local inward tooth or the like.

The invention claimed is:

1. A system for marking a non-human biological object and removing a sample of the biological object, the system comprising:
   a first tag part,
   a second tag part,
   a pin having a first end and a second end, which pin is connected to the first tag part by the first end and which pin is provided with a head at the second end,
   a sample removing stopper which, while attaching the tag parts on the biological object, is positioned on the head of the pin,
   wherein the stopper has an annular cutter at a front of the stopper, which cutter delimits a sample receiving cavity which is open at said front,
   wherein the second tag part is provided with a passage for the stopper and the head of the pin,
   a sample container with an introduction opening for introducing into the sample container the stopper and the sample of the object that has been cut by the cutter, which sample container is attached to the second tag part via a releasable connection, in such a manner that the introduction opening of the sample container and the passage of the second tag part lie in line,
   the system, in use, allowing the pin to be pressed through a part of the biological object, thereby cutting with the cutter a sample from the object, said sample being at least partly received in the sample receiving cavity, and the stopper and the head passing through the passage of the second tag part, as a result of which the first and second tag parts are attached to one another and to the biological object via the pin, the stopper and the sample being introduced into the sample container, said stopper sealing the introduction opening of the sample container, and
   wherein the region of the passage of the second tag part is provided with a sample fixating spike member having a spike, the sample fixating spike member being secured in an initial position thereof to the second tag part such that when the cutter is pressed onto one side of the object the spike is directed towards the sample receiving cavity of the stopper and engages on the opposite side of the sample to be removed from the object thereby fixating said sample to be removed, and the sample fixating spike member being movable away from said initial position into the sample container under the load of the sample when the cutter is pressed onto the opposite side of the object.

2. The system according to claim 1, wherein the sample fixating spike member is secured in an initial position thereof to the second tag part via a temporary retaining connection, such that when the cutter is pressed onto one side of the object and the sample presses onto the spike member, said spike member is pressed from its initial position to slide into the sample container.

3. The system according to claim 1, wherein the sample container has an open, non-sealed introduction opening, and wherein the spike member is embodied as a closure of the passage in the second tag part when the spike member is in its initial position.

4. The system according to claim 1, wherein the spike member has a body with a base and a spike with a tip, wherein, in the initial position, the base is recessed in the passage with respect to the entry opening of said passage for the stopper and the head.

5. The system according to claim 4, wherein, in the initial position, the tip of the spike member is located in or near a plane of the entry opening.

6. The system according to claim 1, wherein the spike member has a base that is adapted to slidingly fit in the sample container.

7. The system according to claim 1, wherein the spike member is embodied as an openable capsule forming at least one sealed compartment therein filled with a functional compound, said capsule being adapted to open upon introduction of the spike member, sample, and stopper into the sample container, thereby bringing said functional compound in communication with the sample.

8. The system according to claim 1, wherein, in the initial position, the spike member is secured via one or more frangible bridges to a retaining ring embedded in the second tag part or to a retaining ring clamped between the second tag part and the sample container, said one or more frangible bridges breaking to allow the spike member to move away from its initial position.

9. The system according to claim 1, wherein, in the initial position, the spike member is clampingly retained in the passage opening and/or in the sample container.

10. The system according to claim 1, wherein, in the initial position, the spike member is secured via one or more deformable connection members said one or more deformable connection members deforming under load applied by the sample onto the spike member and thereby releasing the spike member.

11. The system according to claim 1, wherein the spike member is at least partly made of transparent plastic.

12. The system according to claim 1, wherein the spike member has a body with a base and a tip, wherein the effective height of the spike member above the base is at least 3 millimeters.

13. The system according to claim 1, wherein the spike member has a conical portion having an outer diameter reducing towards the tip of the spike member.

14. The system according to claim 1, wherein the spike member has a base and wherein the sample container has an abutment for said base, the spike member being slideable towards said abutment upon introduction of the spike member, sample, and stopper into the sample container so as to contact said abutment.

15. The system according to claim 1, wherein the spike member is embodied as an openable capsule forming at least one sealed compartment therein filled with a functional compound, said capsule being adapted to open upon introduction of the spike member, sample, and stopper into the sample container, thereby bringing said functional compound in communication with the sample, wherein the spike member has a base and wherein the sample container has an abutment for said base, the spike member being slideable towards said abutment upon introduction of the spike member, sample, and stopper into the sample container so as to contact said abutment, and wherein said capsule is embodied to open upon contact of the spike member with said abutment.

16. The system according to at least claim 1, wherein the spike member is embodied as an openable capsule forming at least one sealed compartment therein filled with a functional compound, said capsule being adapted to open upon introduction of the spike member, sample, and stopper into the sample container, thereby bringing said functional compound in communication with the sample, and wherein the said sample container includes one or more piercing members arranged to pierce said capsule upon introduction of the spike member, sample, and stopper into the sample container.

17. The system according to at least claim 1, wherein the spike member is embodied as an openable capsule forming at least one sealed compartment therein filled with a functional compound, said capsule being adapted to open upon introduction of the spike member, sample, and stopper into the sample container, thereby bringing said functional compound in communication with the sample, and wherein the capsule slidingly fits in said sample container, and wherein said capsule is embodied to open on a side opposite from the spike member, and wherein one or more communication passageways are present between the capsule and the sample container, thereby establishing communication between the sample on one side of the spike member and the functional compound.

18. The system according to claim 1, wherein the spike member is embodied as a brittle component that crumbles or shatters under the pressing load exerted thereon by the sample after having initially resisted said loading.

19. A method for marking a non-human biological object and taking a sample of the non-human biological object, in which use is made of a system of claim 1,
wherein the method comprises pressing the pin through a part of the biological object, thereby cutting with the cutter a sample from the object, said sample being at least partly received in the sample receiving cavity, and the stopper and the head passing through the passage of the second tag part, as a result of which the first and second tag parts are attached to one another and to the biological object via the pin, the stopper and the sample being introduced into the sample container, said stopper sealing the introduction opening of the sample container, and
wherein, when the cutter is pressed onto one side of the object, the spike is directed towards the sample receiving cavity of the stopper and engages on the opposite side of the sample to be removed from the object thereby fixating said sample to be removed, and the sample fixating spike member is moved away from said initial position into the sample container under the load of the sample when the cutter is pressed onto the opposite side of the object.

20. The method according to claim 19, wherein said non-human biological object is the ear of an animal.

21. A system for marking a non-human biological object and removing a sample of the biological object, the system comprising:
a first tag part,
a second tag part,
a pin having a first end and a second end, which pin is connected to the first tag part by the first end and which pin is provided with a head at the second end,
a sample removing stopper which, while attaching the tag parts on the biological object, is positioned on the head of the pin,
wherein the stopper has an annular cutter at a front of the stopper, which cutter delimits a sample receiving cavity which is open at said front,
wherein the second tag part is provided with a passage for the stopper and the head of the pin,
a sample container with an introduction opening for introducing into the sample container the stopper and the sample of the object that has been cut by the cutter, which sample container is attached to the second tag part via a releasable connection, in such a manner that the introduction opening of the sample container and the passage of the second tag part lie in line,
the system, in use, allowing the pin to be pressed through a part of the biological object, thereby cutting with the cutter a sample from the object, said sample being at least partly received in the sample receiving cavity, and the stopper and the head passing through the passage of the second tag part, as a result of which the first and second tag parts are attached to one another and to the biological object via the pin, the stopper and the sample being introduced into the sample container, said stopper sealing the introduction opening of the sample container,
wherein the region of the passage of the second tag part is provided with a sample fixating spike member having a spike, the sample fixating spike member being secured in an initial position thereof to the second tag part such that when the cutter is pressed onto one side of the object the spike is directed towards the sample receiving cavity of the stopper and engages on the opposite side of the sample to be removed from the object thereby fixating said sample to be removed, and the sample fixating spike member being movable away from said initial position into the sample container under the load of the sample when the cutter is pressed onto the opposite side of the object, wherein the sample fixating spike member is secured in an initial position thereof to the second tag part via a temporary retaining connection, such that when the cutter is pressed onto one side of the object and the sample presses onto the spike member, said spike member is pressed from its initial position to slide into the sample container, and wherein the sample container has an open, non-sealed introduction opening, and wherein the spike member is embodied as a closure of the passage in the second tag part when the spike member is in its initial position.

* * * * *